(12) United States Patent
Holland

(10) Patent No.: US 7,408,145 B2
(45) Date of Patent: Aug. 5, 2008

(54) LIGHT SENSING INSTRUMENT WITH MODULATED POLYCHROMATIC SOURCE

(76) Inventor: Kyle Holland, 5011 S. 73rd St., Lincoln, NE (US) 68516

( * ) Notice: Subject to any disclaimer, the term of this patent is extended or adjusted under 35 U.S.C. 154(b) by 332 days.

(21) Appl. No.: 10/703,256

(22) Filed: Nov. 7, 2003

(65) Prior Publication Data
US 2005/0098713 A1    May 12, 2005

Related U.S. Application Data

(60) Provisional application No. 60/505,068, filed on Sep. 23, 2003.

(51) Int. Cl.
*G06M 7/00* (2006.01)
*G01J 1/44* (2006.01)
*G01J 1/32* (2006.01)

(52) U.S. Cl. .............. 250/221; 250/214 AL; 250/205

(58) Field of Classification Search ........ 250/226, 250/214 AL, 341.8, 214 B, 221, 339.02, 339.11, 250/214 R, 205, 559.4, 338.1, 458.1–461.1, 250/330, 339.14, 339.01, 361 R, 339.05, 250/339.06, 339.12; 47/1.7; 356/317, 318, 356/417, 447, 445; 417/1.7; 239/170; 382/110
See application file for complete search history.

(56) References Cited

U.S. PATENT DOCUMENTS 3,443,072 A    5/1969 Mori (Continued)

OTHER PUBLICATIONS

Haggar, R.J., Stent, C.J., and Isaac, S., "A prototype hand-held patch sprayer for killing weeds, activated by spectral difference in crop/weed canopies", Agricultural Research Council, Nov. 15, 1982, pp. 349-358.

(Continued)

*Primary Examiner*—Que T. Le
*Assistant Examiner*—Pascal M Bui-Pho
(74) *Attorney, Agent, or Firm*—Kent A. Herink; Emily E. Harris

(57) ABSTRACT

An apparatus is described for assessing plant status using biophysical and biochemical properties of the plant remotely sensed by the invention thereby allowing selective monitoring, elimination or treatment of individual plants. In a preferred embodiment, a single polychromatic emitter provides coincident light beams; one beam substantially in the visible portion of the spectrum (400 nm to 700 nm) and the other in the near infrared (NIR) portion of the spectrum (700 nm to 1100 nm). This light beam illuminates a small surface area on the ground, which may be bare ground, desired plants or undesired weeds. The beam of light may be focused, collimated or non-focused. A detector array, usually composed of a visible detector and a NIR detector, detects portions of this polychromatic light beam reflected by the surface area and provides a signal indicative of whether the detected light was reflected by a plant or by some non-plant object such as soil. A controller analyzes this signal and, assuming a plant is detected, responds by activating a device to take some action with respect to the plant or stores the analyzed signal with corresponding DGPS position in the controller's memory for later analysis. A number of actions may be taken by the controller. For instance, if the plant is a weed, the desired action might be to spray herbicide on the weed. Or, if the plant is a crop that is determined to be lacking in nutrient, the desired action may be to apply fertilizer. Additionally, if the plant under test is a turf landscape, such as found on golf courses and sporting fields, plant biomass may be mapped and geo-located using GPS for later, comparative analysis.

18 Claims, 14 Drawing Sheets

Block diagram of typical sensor embodiment.

U.S. PATENT DOCUMENTS

| | | | |
|---|---|---|---|
| 3,910,701 | A | 10/1975 | Henderson et al. |
| 4,055,768 | A | 10/1977 | Bromberg |
| 4,369,886 | A | 1/1983 | Lane et al. |
| 4,518,253 | A | 5/1985 | Takahashi |
| 4,628,454 | A | 12/1986 | Ito |
| 4,926,170 | A | 5/1990 | Beggs et al. |
| 4,986,665 | A * | 1/1991 | Yamanishi et al. .......... 356/402 |
| 5,025,150 | A | 6/1991 | Oldham et al. |
| 5,144,767 | A | 9/1992 | McCloy et al. |
| 5,296,702 | A * | 3/1994 | Beck et al. ................. 250/226 |
| 5,389,781 | A | 2/1995 | Beck |
| 5,585,626 | A | 12/1996 | Beck et al. |
| 5,763,873 | A | 6/1998 | Beck et al. |
| 5,789,741 | A | 8/1998 | Kinter |
| 5,809,440 | A | 9/1998 | Beck et al. |
| 5,833,144 | A | 11/1998 | Kinter |
| 5,837,997 | A | 11/1998 | Beck |
| 6,160,902 | A * | 12/2000 | Dickson et al. ............. 382/110 |
| 6,393,927 | B1 | 5/2002 | Biggs |
| 6,596,996 | B1 * | 7/2003 | Stone et al. .............. 250/341.8 |
| 2004/0119020 | A1 * | 6/2004 | Bodkin ....................... 250/353 |

OTHER PUBLICATIONS

Hooper, A.W., Harries, G.O., & Ambler, B., "A photoelectric sensor for distinguishing between plant material and soil", J. agric. Engng. Res. 1976, 21, pp. 145-155.

Industrial Control Applications, Mar. 1991. Infrared sensing and data transmission fundamentals. Motorola. DL412/D, AN1016, pp. 349-354.

Linear and Interface Integrated Circuits. 1988. MC3373 Datasheet. Motorola. pp. 9-43 to 9-46.

Gage, S., Evans, D., Hodapp, M. and Sorensen, H. 1977 Optoelectronics Applications Manual. McGraw-Hill Book Company.

Seeing the Light of Nitrogen. Mid-Feb. 1996. Nebraska Farmer. pp. 14, 15 and 20.

Tools with Eyes. Mid-Mar. 1989. Farm Journal. pp. 16-18.

McCabe, D., "An eye on nitrogen", Precision Ag. Mar. 2004, pp. 21-23.

Searcy, S.W. et al 1990. Measurement of agricultural field location using microwave frequensy triangulation. Computers and Electronics in Agriculture. vol. 4, pp. 209-223.

Thompson, J.F. et al 1991. Potential for automatic weed detection and selective herbicide application. Crop Protection. vol. 10 Aug. 1991, pp. 254-259.

Ritchie, J.C et al. 1992. Airborne laser measurements of rangeland canopy cover and distribution. J. Range Manage. 45:189-193.

Aronson, A. H. 1977 Low-level Measurements—8 Lock-in and carrier amplifiers. Measurements and Data Corporation. pp. C1-C15.

* cited by examiner

Vegetative reflectance curve

Vegetative reflectance curves for four different N-rates

Chlorophyll excitation by blue and red light.

Fluorescence excitation and emission.

Sensor enclosure diagram

Block diagram of typical sensor embodiment.

Monochromatic LED Emission.

Polychromatic LED Emission

Detector trimming techniques for a two detector array

Vegetative reflectance curve depicting red-edge region.

Sensor-based mapping system

Sensor-based variable-rate applicator system.

Variable rate applicater implementation depicting sensor-to-nozzle distance D needed to average plant canopy periodicity and leaf orientation.

LIGHT SENSING INSTRUMENT WITH MODULATED POLYCHROMATIC SOURCE

This application claims priority to U.S. Patent Application Ser. No. 60/505,068, filed Sep. 23, 2003.

BACKGROUND OF THE INVENTION

1. Field of the Invention

This invention relates to a structure and a method for the detection of objects in particular the determination of plant status via remote sensing of plant biomass and plant biochemical properties for the purposes of mapping and applying agricultural products e.g. nitrogen based fertilizer.

2. Description of Related Art

In order to manage our natural resources in an efficient and cost-effective manner, producers and turf professionals need a way in which to measure and assess the health and performance of their landscapes. For example, the need to know when and how much fertilizer (nitrogen) and other nutrients to apply to a plant to elicit the appropriate growth response is primarily guess work to the producer. Because nitrogen is required by the plant in the greatest quantities and because nitrogen is rather mobile in soils, producers have practiced a one time application of nitrogen to cover the crops need for the entire growing season. However, over application of nitrogen on agricultural and commercial landscapes has resulted in the contamination of ground and surface waters. The primary vectors for water contamination are run-off and leaching. Nitrate-nitrogen is the most common contaminant found in U.S. groundwater. Nitrate contamination is increasing both in area and concentration, particularly beneath landscapes dominated by corn production. It is estimated that $1.8 \times 10^9$ kilograms of nitrates wash into the Gulf of Mexico from the Mississippi River basin each year. Of this amount, 55% of the nitrogen released into the basin can be attributed to agricultural fertilizers with only a 3% contribution attributable to non-agricultural fertilizer application primarily on turf for lawns and recreational land (CAST, 1999).

Techniques to remotely measure crop status include the use of a spectroradiometer and other instruments (Bausch et al. 1994; Chappelle et al. 1992; Maas and Dunlap, 1989), aerial photography (Benton et al, 1976), and satellite imagery.

The techniques listed above are not without their limitations. For example, early research by Resource21™ determined that during the optimal fly over times between 10 a.m. and 11 a.m. for satellite imaging, cloud cover had adverse affects on visibility. It was found that during the 10 am to 11 am time frame, fields in Colorado were visible approximately 80% of the time while eastern Nebraska fields were visible approximately 50% of the time. This trend in decreased visibility continued the farther east that data was collected. Also, spatial resolution for satellite imagery is poor (Landsat, 20 meter and panchromatic, 10 meter). Similar problems plague aerial photographic methods as well. While aerial imagery has better spatial resolution (typically less than 3 meters) than satellite imaging, partial cloud cover can shade sections of fields giving biased or incorrect reflectance measurements. Both techniques, however, suffer from the need for extensive data processing (performed by third party providers at high cost and long lead time) and geo-referencing issues. Even with spectroradiometric methods using sunlight as the ambient light source, cloud cover and time of day (8 a.m. to 8 p.m.) demands limit the mainstream acceptance of the technology for addressing the nitrogen rate over-loading problem. What is needed is an on-the-go type sensor that overcomes the time of day and fair-weather issues surrounding the aforementioned measurement techniques.

In certain crops or plant varieties, nutrient deficiencies constitute only part of the management problem. In particular, the basic problem of determining or monitoring plant status with respect to stress whether it stems from nutrient, water, pest, disease, or otherwise is of primary concern. For instance, turf stress determination is of major concern for the turf manager. Earlier detection can protect the health of the grass but also reduce the cost of restoring the badly damaged turf to good health. Turf stress can be due to many causes such as water, pest, nutrient, heat, disease, and the like. By detecting changes in the turf landscape early, turf quality can be maintained and costly restoration operations can be reduced or eliminated. On the other hand, being able to control the degree of stress is important for some producers. Grape producers, for example, like to control the degree of water stress prior to harvesting in order to control disease and increase the sugar content of the grape.

SUMMARY OF THE INVENTION

The new sensor of the present invention overcomes the time-of-day and fair weather limitations of passive technologies by incorporating its own radiant source and by rejecting the influence of ambient light on the measured canopy reflectance. Unlike passive sensor technology, this sensor will be able to operate under completely dark or full sun conditions. Additionally, the new sensor apparatus is an improvement both in performance and cost over competing active-sensor technologies commercially available.

As discussed above, the invention presented here will be advantageous in a number of commercial applications. For site specific agricultural applications, the developed sensor would allow the producer to reduce the amount of nitrogen fertilizer applied to a crop or facilitate spoon-feeding the crop during the growing season, thus having the potential for lowering production costs and enhancing environmental quality. Also, by being able to determine the appropriate fertilizer needs of the crop at any given location in the field, the producer can apply only the fertilizer needed to prevent yield loss or degradation of product quality (i.e., protein content in wheat and barley or sugar content in sugar beets). Subsequently, decreased fertilizer rates will substantially lower nitrogen runoff and leaching losses, which will improve the health of our watersheds, waterways, lakes, and oceans. In addition, data produced by the sensor may be used to produce relative yield maps for forecasting crop production. Also, the fluorescence capability of the sensor can be used in conjunction with reflectance measurements to improve biomass determination. The chlorophyll fluorescence capability of the sensor has the potential to determine plant stress and disease conditions, which are useful indicators when selecting crop hybrids for commercialization. As for turf grass applications, the sensor technology would allow turf managers to map changes occurring on turf landscapes or for monitoring the status of turf quality.

In accordance with the present invention, structures and methods are provided for assessing plant status using biophysical and biochemical properties of the plant remotely sensed by the invention thereby allowing selective monitoring, elimination or treatment of individual plants. In one embodiment of this invention, a single polychromatic emitter provides coincident light beams; one beam substantially in the visible portion of the spectrum (400 nm to 700 nm) and the other in the near infrared (NIR) portion of the spectrum (700 nm to 1100 nm). This light beam illuminates a small surface area on the ground, which may be bare ground, desired plants or undesired weeds. The beam of light may be focused, collimated or non-focused. A detector array, usually composed of a visible detector and a NIR detector, detects portions of this polychromatic light beam reflected by the surface area and provides a signal indicative of whether the detected light was reflected by a plant or by some non-plant object such as soil. A controller analyzes this signal and, assuming a plant is detected, responds by activating a device to take some action with respect to the plant or stores the analyzed signal with corresponding DGPS position in the controller's memory for later analysis. A number of actions may be taken by the controller. For instance, if the plant is a weed, the desired action might be to spray herbicide on the weed. Or, if the plant is a crop that is determined to be lacking in nutrient, the desired action may be to apply fertilizer. Additionally, if the plant under test is a turf landscape, such as found on golf courses and sporting fields, plant biomass may be mapped and geo-located using GPS for later, comparative analysis.

In another unique embodiment of this invention, two light emitters provide selectively modulated monochromatic light beams of different wavelengths. One light beam is preferably in the visible portion of the spectrum and the other is in the NIR portion of the spectrum. These light beams illuminate a small surface area on the ground which, again, may be bare ground, desired plants or undesired weeds. A detector array which, in a preferred embodiment, may comprise a visible detector and a NIR detector, detects portions of the monochromatic light beams reflected by the surface area and provides a signal indicative of whether the detected light was reflected by a plant or by some non-plant object such as soil. Additionally, the visible light source may be utilized to excite chlorophyll fluorescence from the plant. The emission wavelength of the fluorescence emission is detected using the NIR channel. The fluorescence signal contains information allowing the invention to distinguish between plant from soil (most soils do not fluoresce) or to relate the plant's status to stress or disease. The signal produced can be integrated into a controller and processed as in the previous embodiment.

When incorporated into variable rate applicator and/or sprayer systems, the present invention significantly reduces the use of fertilizers or herbicides by precisely applying agricultural products to individual plants to be treated or eliminated. Moreover, the present invention is operable under a wide variety of conditions including cloudy conditions, bright sunlight, artificial illumination, or even total darkness. The advantage to the producer is that field operations do not have to be timed to daytime sunlight hours for operation.

All embodiments of the invention can be used in two primary ways. The first method of use includes the application of the invention to handheld instrumentation. Here the invention is utilized to measure plant canopies held in hand by a producer, turf manager, researcher, and the like. The invention includes the use of GPS for geo-referencing data collected by the invention. A second method of use includes applications where the sensor is mounted on a moving object such as a tractor, mower, center pivot/linear irrigator, or the like. Again, data may be geo-referenced using GPS for mapping and data layer (GPS maps, soil maps, etc.) integration. Problem areas can be logged and reviewed later by the producer or land manager for analysis and site management decisions.

An object of the invention is to provide a sensor for remotely sensing plant status using biophysical and biochemical properties of the plant thereby allowing selective monitoring, elimination, or treatment of individual plants.

This and other objects of the invention will be made apparent to those skilled in the art upon a review of this specification, the associated drawings and the appended claims.

DETAILED DESCRIPTION OF PREFERRED EMBODIMENTS

Figure 1:
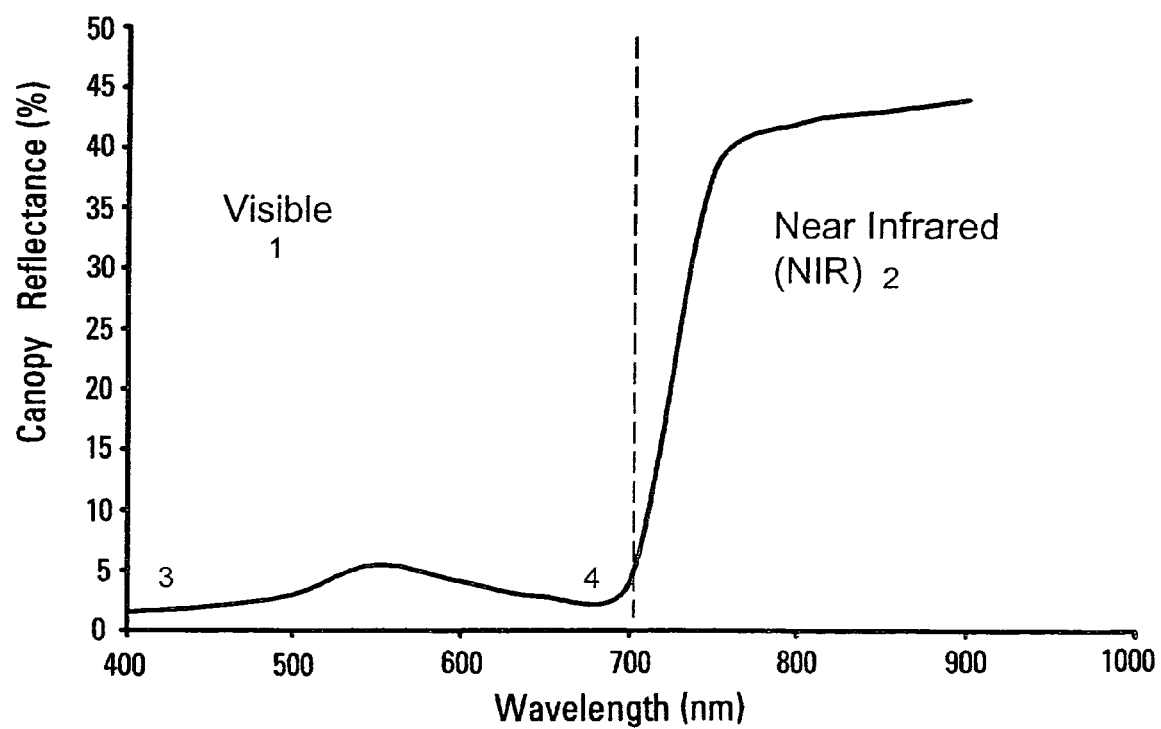
FIG. 1 illustrates plant reflectance curves over the visible and near infrared portion of the spectrum.

The following contains a description for a sensor that measures plant canopy and soil reflectance independent of ambient illumination levels. More generally, the sensor could be used in any situation where a particular surface condition or feature needed to be remotely detected under variable ambient light conditions. The sensor can be used in stand-alone instrumentation configurations or in a network of sensors mounted to a vehicle or moving apparatus for on-the-go remote sensing applications. The following description of the invention is meant to be illustrative and not limiting. Other embodiments will be obvious in view of this invention.

The positive relationship between leaf greenness and crop nitrogen (N) status means it should be possible to determine crop N requirements based on reflectance data collected from the crop canopy (Walberg et al., 1982; Girardin et al., 1985; Hinzman et al., 1986; Dwyer et al., 1991) and leaves (McMurtrey et al., 1994). Plants with increased levels of N typically have more chlorophyll (Inada, 1965; Rodolfo and Peregrmna, 1962; Al-Abbas et al., 1974; Wolfe et al., 1988) and greater rates of photosynthesis (Sinclair and Horie, 1989). Hence, plants that appear a darker green are perceived to be healthier than N deficient plants. Chlorophyll in leaves absorbs strongly in the blue 3and red 4 regions of the visible spectrum (Region 1, 460 nm and 670 nm) and reflects/transmits light in the green region (550 nm) and near infrared region (Region 2), see FIG. 1. Blackmer et al. (1994a,b,c) used a spectroradiometer to characterize the differences in light reflected from corn canopies receiving different N treatments, see FIG. 2. They found a strong relationship between green light (550 nm) and fertilizer N rate. In addition, green light reflectance from corn during the late milk stage (R4 to R5) was highly correlated with grain yield ($r^2$=0.98, ten N rates for one hybrid). As a result, it is the relationship between leaf greenness (reflected green light) and chlorophyll content (absorbance) which makes it possible to remotely sense or measure leaf greenness and obtain an indication of chlorophyll concentration and plant N status. A useful feature of measuring leaf greenness or chlorophyll content is that greenness does not generally increase with luxury consumption of N. Plants achieve maximum greenness regardless of the amount of excess N supply. Thus, in order to create a measure for crop N status, producers can establish N-adequate reference areas by applying in those areas enough extra N fertilizer to guarantee N is non-limiting. One can then determine N status and/or detect deficiency by comparing greenness values between the reference area and the area in question.

To demonstrate the capabilities of the sensor for assessing crop status with respect to nutrient sufficiency, the invention was tested on 5 N-rate treatments of 34-0-0 ammonium nitrate fertilizer (0, 50, 100, 150 and 200 lb/acre) for 4 different corn hybrids. Chlorophyll data were obtained by USDA-ARS personnel using Minolta SPAD meters. SPAD data were collected from the ear level leaves of corn plants in a corn rotation. Thirty SPAD meter samples were taken for each treatment in the study. Nitrogen rate order was randomized within each hybrid. The sensor was mounted onto a high clearance vehicle and was driven through the field at velocities ranging from 2 to 4 mph. Two measurement runs through the rotation study were conducted, each with two replications. The first run through the test plots set the field of view of the sensor to measure the upper portion of the corn plant just below the tassel. The second run through the corn study positioned the sensor to measure the plant canopy at ear level. The crop was at the R1 growth stage (early blister) at the time of sampling. Table 1 summarizes the sensor's performance for the two runs through the test plots with correlation between SPAD and GNDVI measurements for each replication listed.

TABLE 1

Prototype sensor GNDVI vs. SPAD meter for N-rates of 0, 50, 100, 150 and 200 lb/acre on four corn hybrids.

| | Position | | | |
| --- | --- | --- | --- | --- |
| | Below Tassel Level | | Ear Leaf Level | |
| Hybrid | $R^2$ (PASS 1) | $R^2$ (PASS 2) | $R^2$ (PASS 1) | $R^2$ (PASS 2) |
| H1 | 0.99 | 0.81 | 0.97 | 0.97 |
| H2 | 0.90 | 0.95 | 0.98 | 0.96 |
| H3 | 0.86 | 0.96 | 0.85 | 0.88 |
| H4 | 0.97 | 0.99 | 0.97 | 0.94 |

Corn Hybrid

H1 P32R42  H2 P33B50
H3 P33G26  H4 P33P66

Very good correlation with SPAD meter readings was obtained. Table 2 summarizes the sensor's performance for the two runs through the test plots with correlation between N-rate and GNDVI measurements for each replication listed.

TABLE 2

Prototype sensor GNDVI vs. N-rate for N-rates of 0, 50, 100, 150 and 200 lb/acre on four corn hybrids.

| | Position | | | |
| --- | --- | --- | --- | --- |
| | Below Tassel Level | | Ear Leaf Level | |
| Hybrid | $R^2$ (PASS 1) | $R^2$ (PASS 2) | $R^2$ (PASS 1) | $R^2$ (PASS 2) |
| H1 | 0.87 | 0.91 | 0.78 | 0.83 |
| H2 | 0.85 | 0.94 | 0.81 | 0.74 |
| H3 | 0.80 | 0.72 | 0.93 | 0.88 |
| H4 | 0.72 | 0.84 | 0.91 | 0.92 |

Corn Hybrid

H1 P32R42  H2 P33B50
H3 P33G26  H4 P33P66

Good correlation with N-rate was obtained. The lower correlation numbers of GNDVI vs. N-rate than GNDVI vs. SPAD could be due to the uncertainty of the residual soil $NO_3$ available to the plant for nutrient assimilation.

Note also, when leaf greenness starts to decrease, changes in the plants condition with respect to various types of stress can be assessed. This is oftentimes associated with a decrease in foliage biomass. In turf application, decreased greenness and biomass is indicative in either diminished tiller density and/or the onset of stress and disease. By routinely measuring biomass and greenness during mowing and other turf management operations, changes in turf quality, whether abrupt or gradual, can be monitored throughout the growing season. Earlier detection of turf damage and disease can save thousands of dollars in restoration costs.

On turf plots, the invention was able to distinguish between poor performing turf and healthier turf within the same cultivar. Diseased or stressed cultivars exhibited different reflectance and fluorescence characteristics from those of healthy cultivars. The fluorescence capability of the invention, in conjunction with the basic reflectance measurement capability, can be used together to determine trends in turf growing conditions or to determine early onset of disease and stress. This capability was tested on turf plots. It was determined that the invention was able to distinguish between poor performing turf and healthier turf within the same cultivar. Diseased or stress cultivars exhibited different reflectance and fluorescence from those of healthy cultivars. Table 3 lists the GNDVI and fluorescence values for the cultivar plots tested. From the data shown in Table 3, the first turf plot (126) suffering from disease can be distinguished from the other two plots in the cultivar. The health status of this plot is reflected in the sensor data shown in Table 3. The stress signature, as indicated by the data for this plot, is not only a reduction of GNDVI, but also reduced fluorescence. The other two plots in this cultivar are healthy and have similar sensor signatures. The three Langara cultivar plots are healthy and exhibit similar sensor signatures as shown in Table 3.

TABLE 3

Figure 13:
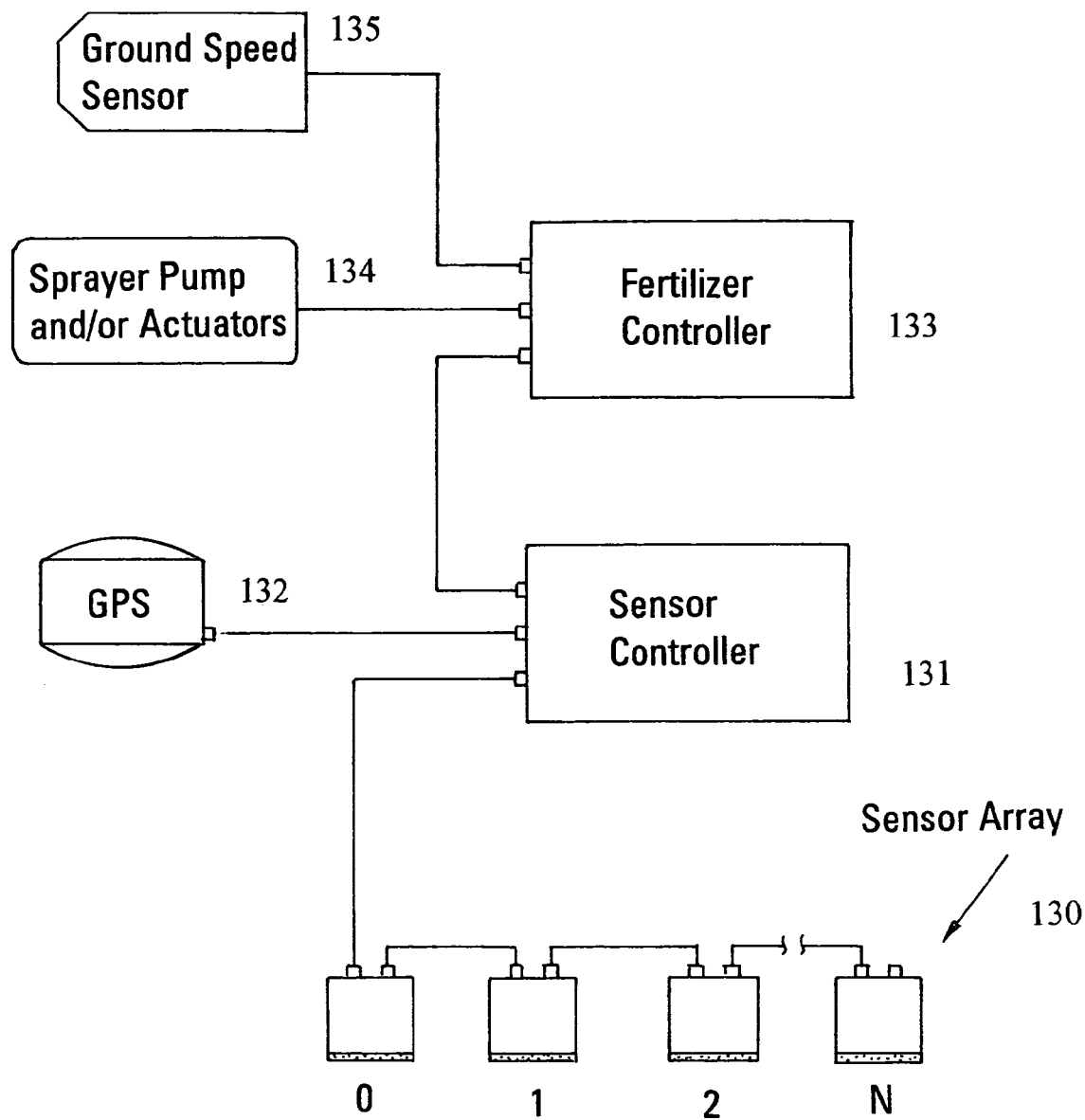
FIG. 13 shows diagrammatically a sensor based variable-rate applicator system.
Figure 14:
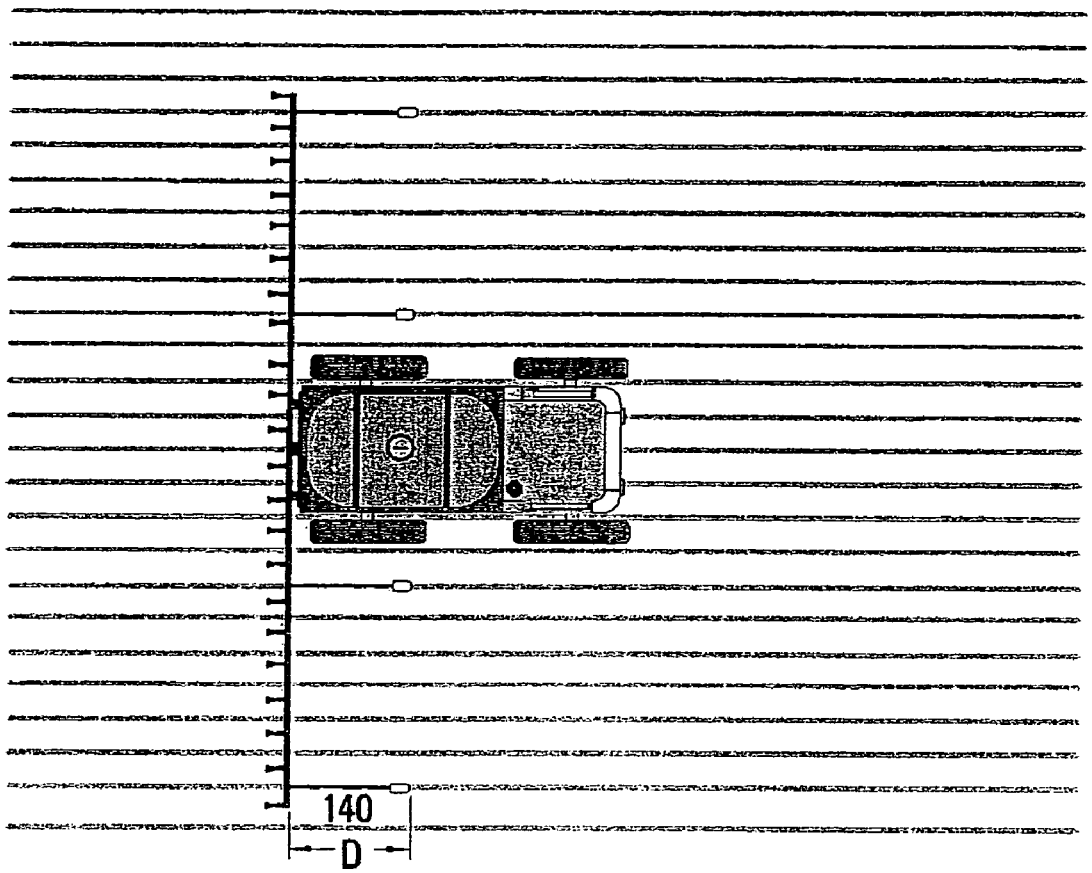
FIG. 14 illustrates the necessary sensor-to-spray nozzle separation for compensating for plant canopy periodicity and random leaf orientation.

Sensor measurements for turf cultivars shown in FIG. 13 and 14.

| Cultivar | Plot # | GNDVI | Fluorescence | Status |
| --- | --- | --- | --- | --- |
| Chicago II | 126 | 0.227 | 717 | D |
| Chicago II | 199 | 0.372 | 905 | H |
| Chicago II | 374 | 0.381 | 892 | H |
| Langara | 150 | 0.389 | 1068 | H |

TABLE 3-continued

Sensor measurements for turf cultivars shown in FIG. 13 and 14.

| Cultivar | Plot # | GNDVI | Fluorescence | Status |
|---|---|---|---|---|
| Langara | 196 | 0.379 | 1038 | H |
| Langara | 498 | 0.390 | 1124 | H |

D = Diseased,
H = Healthy

Another application of the invention relates to object detection, in particular to weed locating. For example, consider a field that has been tilled and has a crop planted. At this time only stubble from the past harvested crop is exposed and weeds have sprouted. It may be desirable to kill the weeds at this stage in the growing cycle by an application of herbicide. Since the population of weeds is sparse and their location is randomly placed within the field, a sprayer operator would have to apply herbicide to the whole field. As a result, considerable amounts of herbicide would be wasted on areas of the field that did not need spraying. Such blanket spraying is expensive and may involve undesirable environmental impact. Techniques are thereby sought to reduce the amount of herbicide wasted. The invention of this patent provides a selective way, when integrated into a sprayer implement, in which to apply herbicide based on the detection of a weed as distinguished from soil or background characteristics. It is obvious from the above examples that the technology can be readily applied to other types of plants.

The new sensor technology of the present invention overcomes the time of day and fair weather limitations of current passive spectroradiometric technologies by incorporating its own modulated, radiant light source. The invention improves upon current active sensor technology by incorporation the use polychromatic LED sources and allowing for the measurement of steady-state chlorophyll fluorescence.

Figure 2:
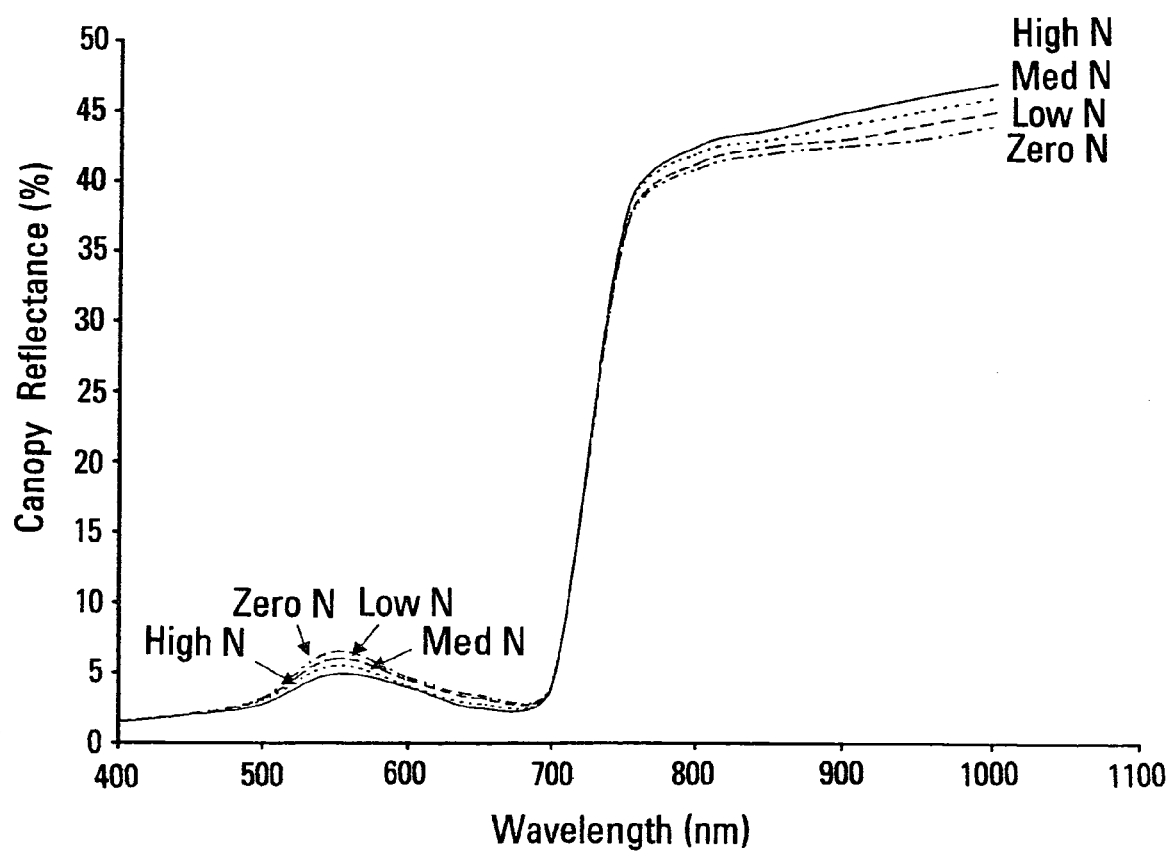
FIG. 2 illustrates the effect of nitrogen rate on the plant reflectance curve over the visible and near infrared portion of the spectrum.

The optical measurement of plant biomass characteristics typically requires a measurement using visible and NIR light. As shown in FIG. 1, visible light is highly absorbed in the visible region 1 of the spectrum (<700 nm). This is due mostly to the plant's need for light in this spectral region to drive its photosynthetic mechanisms. However, in the near infrared portion 2 of the spectrum (>700 nm), the cellular structure of the plant tissue highly reflects. Reflectance values from a plant canopy range from about 2% to 15% for the visible portion of the spectrum and 25 to 80 percent in NIR region of the spectrum. Another interesting phenomenon with respect to plants pertains to chlorophyll fluorescence. Of the photosynthetic energy that the plant absorbs, part of the energy is used for photosynthesis (A), part of the energy is dissipated as heat (D) and the remainder of the energy is re-radiated as chlorophyll fluorescence.

Figure 3:
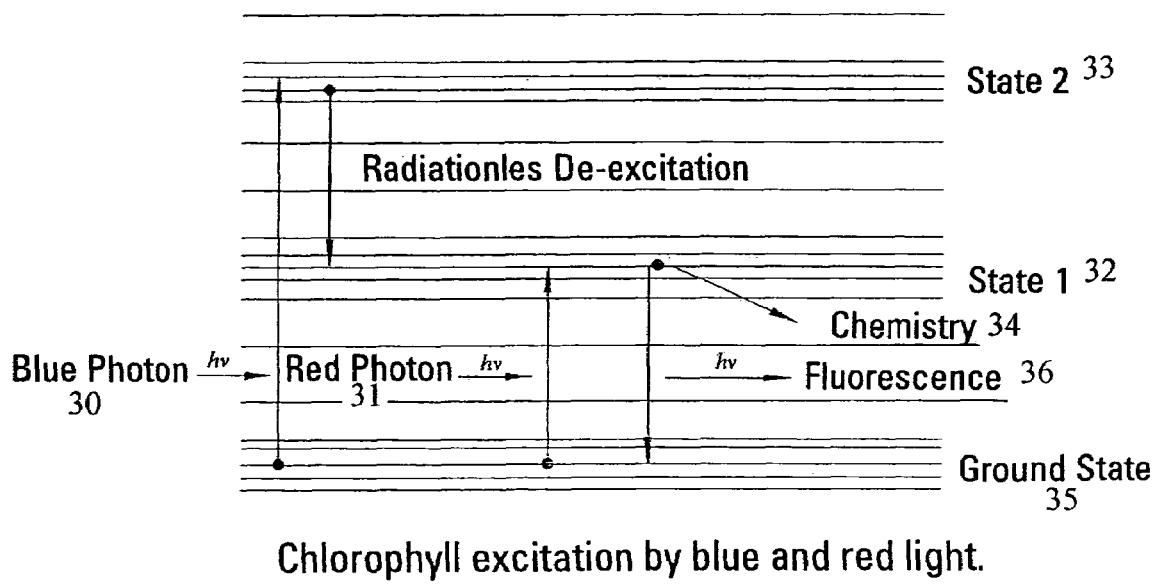
FIG. 3 illustrates the quantum mechanism involved in chlorophyll fluorescence for blue and red light.

The magnitude of the fluorescing light intensity is, depending on the health status of the plant, typically 0.1% to 1% in magnitude to that of the reflecting light intensity signal. Fluorescence occurs when light absorbed by a plant raises electrons, within the chlorophyll molecule, to excited states that fall back to the ground state without contributing to photochemical work. FIG. 3 shows the quantum mechanisms pertaining to chlorophyll fluorescence excitation by blue 30 and red 31 light. A red photon has enough energy to raise an electron to excited state 1 (32). The route for the photon in this situation is either to be utilized for the photochemistry 34 of the plant or to fall directly back to the ground state 35 and subsequently re-emit a photon 36 in the process. A blue photon has enough energy to excite an electron to excited state 2 (33). In this case, the excited electron de-excites through substrates without producing any radiation to excited state 1 (32). At this point, the electron can be utilized for photochemical chemical work or fall to the ground state producing a photon in the process.

Figure 4:
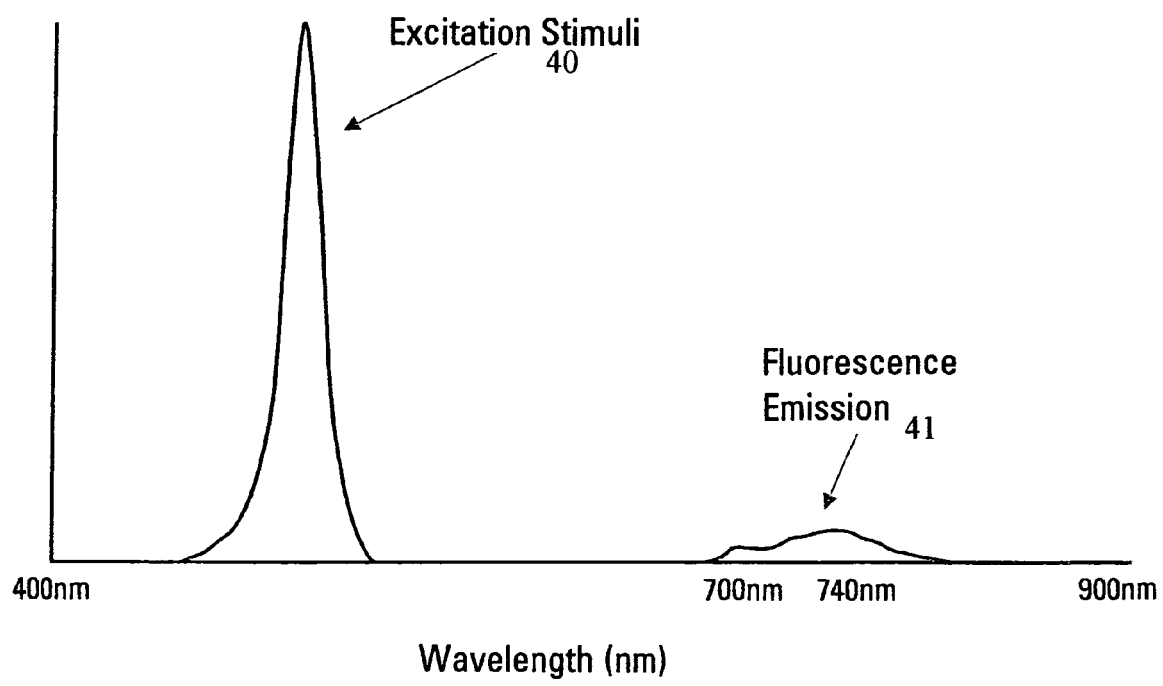
FIG. 4 illustrates the characteristic excitation and emission spectra for chlorophyll fluorescence of a plant. Excitation wavebands are typically less than 650 nm in the visible portion of the spectrum and the emission waveband is in the near infrared spanning from 695 nm to 780 nm.

FIG. 4 shows a graph depicting the excitation 40 and emission 41 spectra for chlorophyll fluorescence. Here a light source with a wavelength less than 680 nm is utilized to excite chlorophyll fluorescence and the subsequently fluorescing light is emitted in the 680 nm to 780 nm portion of the spectrum. Note that from the graph in FIG. 4, fluorescence occurs with a shift towards the red, also known as a Stokes shift. This is because the electron has the opportunity to lose small fractions of energy as heat when it falls back to the ground state through other excited states. As alluded to above, the magnitude of the fluorescing signal available for measurement from a plant canopy is dependent on a number factors that include stress (thermal, water, disease, nutrient, and the like), biomass (how much living plant material is in the field-of-view of the sensor) and the ambient photon flux irradiating the plant. The present invention seeks to exploit both of these phenomena (leaf reflectance and chlorophyll fluorescence) for the purpose of assessing plant status.

Figure 5:
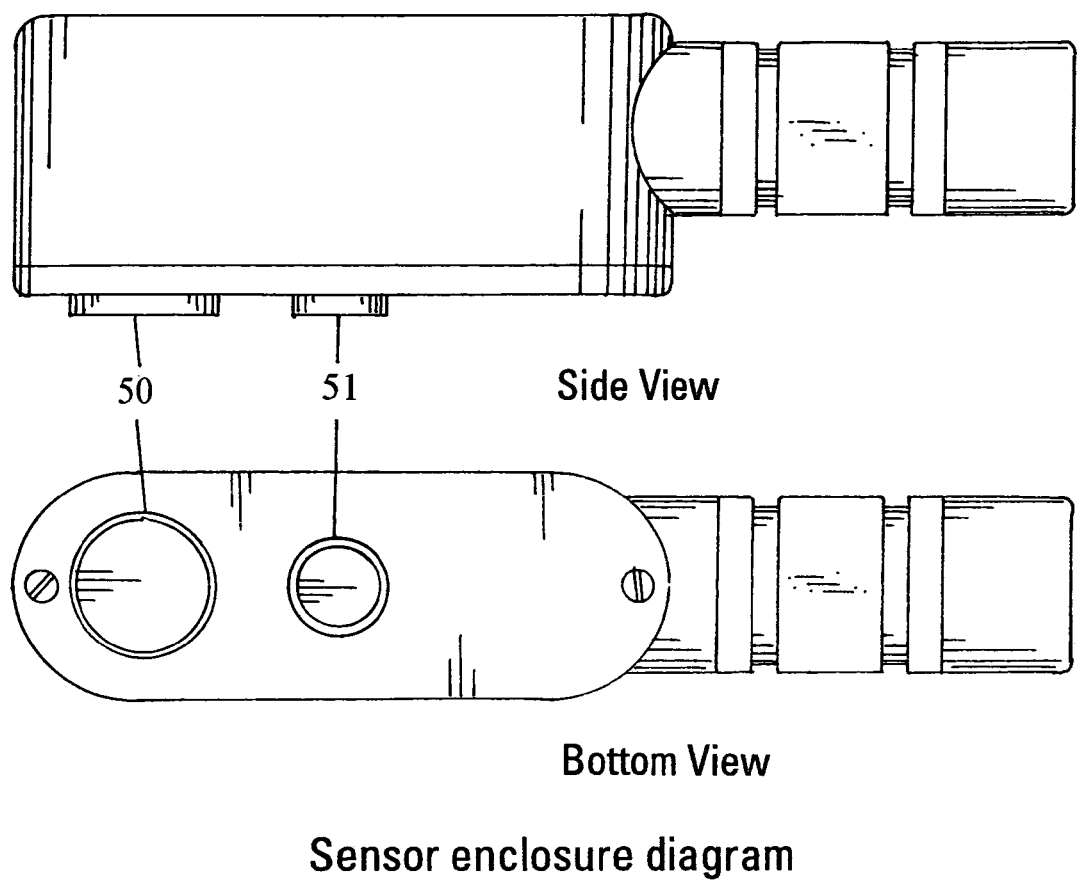
FIG. 5 shows a diagram of a the inventions mechanical enclosure.

FIG. 5 shows a diagram of the sensor enclosure. The enclosure facilitates the protection of the electronic circuitry while providing optical emission and reception ports for the light source and the light detector components, respectively, of the sensor. Port 50 in FIG. 5 is the emitter port of the sensor while port 51 is the detector port of the sensor. Port 50 and port 51 can facilitate various types of optical components to concentrate and collect optical energy. The type of optics used by the sensor can include lens, mirrors, optical flats, filters, and diffusers. The type of optics selected for the emitter and detector optics depends on the application; that is, the required field of view, the height the sensor will be operated above the plant canopy, the required cost of the sensor all may play a part in the design of the sensor's optical arrangement. The sensor can operate at a distance of 1 foot and up to several feet from the plant canopy or surface of interest but is not limited to this specific range. To those skilled in the art it should be readily apparent that fore optics on the emission side and the detection side can take on many forms.

For example, a useful optically adaptation on the detector side of the optical arrangement would be to encapsulate the detector optics (filters and detectors). The outer optical surface would have a convex surface spaced from the plane of the photodiode so as to create an afocal or nearly afocal optical arrangement. This preferred mode of construction improves the optical energy collection performance of the filter/diode combination while sealing the optical path from dust and water vapor condensation.

On the emission side of the sensor, there are a number of ways in which to shape and direct the light beam emitting from the sensor body. For instance, if one wishes to generate a line pattern from the sensors light source, preferably a bank of LEDs, one could place a cylindrical lens in front of this light source spaced appropriately so as to image a line of illumination in the field of view of the detection optics.

Alternately, a circular or ellipsoidal area of irradiance can be produced using only the encapsulation optics of an array of LEDs. In this instance, the beam pattern produced by the source is defined by the spatial irradiance distribution of each individual LED. No additional collimation or focusing optics is incorporated. Encapsulated LEDs can be purchased commercially that have spatial distribution angles of 4 degrees to almost 180 degrees. Most preferably, it is best to collimate the light emitted from an LED in order to maintain a light beam with relatively constant projection over distance. In this case the LED or LED array would be spaced an appropriate distance from a convex lens (or concave mirror) to form an afocal or nearly afocal optical system. The resulting optical system will produce a light beam that will collimated along the optical axis of the light source resulting in areas of illumination with high irradiance. The intensity of this projected beam will vary with the inverse of the distance squared from the sensor's collimating lens.

Figure 6:
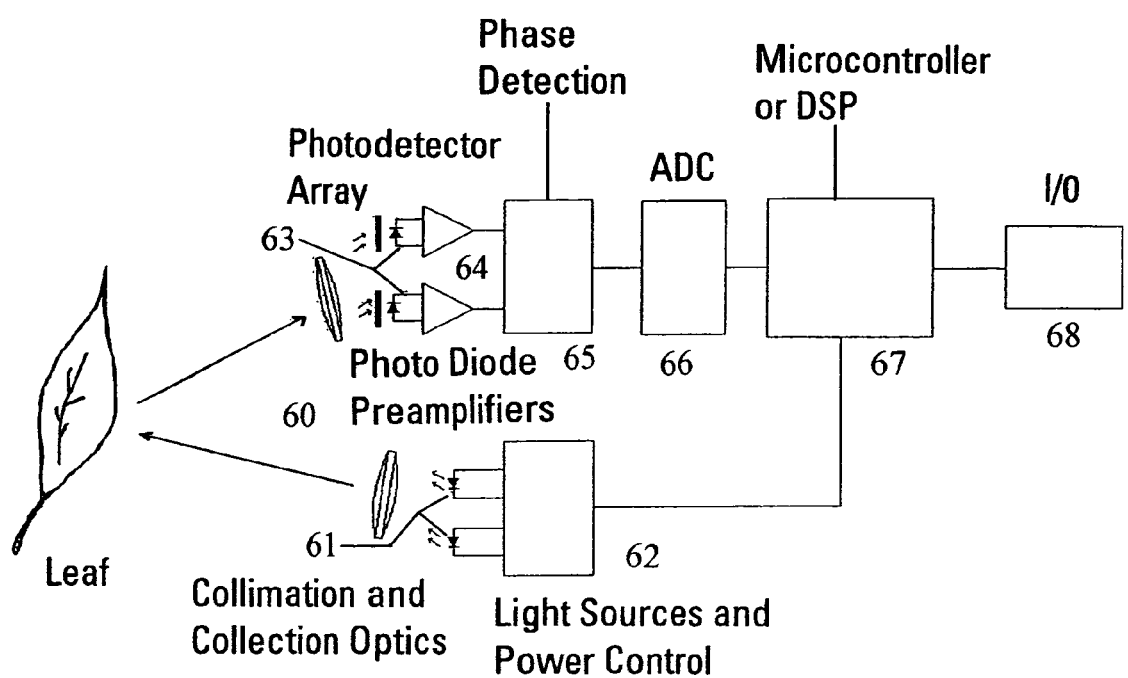
FIG. 6 shows the functional block diagram of a typical sensor embodiment.

FIG. 6 shows a system diagram typical for the many embodiments of the invention. The sensor is composed of optics to facilitate optical energy collimation and collection, a modulated light source 61 comprised of one or many banks of polychromatic LEDs and/or monochromatic LEDs or laser diodes (LD) with associated modulated driver and power control electronics 62, multichannel photodetector bank 63, high-speed preamplifier array with ambient light cancellation 64, a phase sensitive signal conditioning 65 and data acquisition circuitry 66, and a microcontrol unit (MCU) or digital signal processor (DSP) 67 and an input/output interface 68 to communicate sensor data to an operator or controller. These system elements will be discussed in the following.

The light source for the invention is most preferably composed of light emitting diodes. LEDs are convenient light sources for this type of invention for a number of reasons. First, LEDs are available in a number of colors useful for making plant biomass and pigment measurements. LEDs are readily available in colors spanning from deep violet (395 nm) to near infrared (940 nm). Most recently, the UV LEDs have been developed in the 350 nm to 370 nm. These particular devices would be useful for stimulating pigment fluorescence in plants as the spectral distribution for pigment fluorescence in plants spans from 400 nm to 550 nm. Another useful class of LEDs has been recently developed for the telecommunications industry. These devices have spectral emissions spanning from approximately 1300 nm to 1550 nm. This range of devices is particularly useful for measuring water stress associated with plants. Second, LEDs are extremely easy to use and can be modulated to megahertz frequencies. Relatively simple electronic driver circuits can be implemented and easily controlled by sensor controller electronics. Last, LEDs have long lifetimes and are rugged. The typical LED will operate between 80,000 and 100,000 hours depending on the quiescent device power and operating temperature range.

LEDs are crystalline materials composed of various transition elements and dopants that include gallium, arsenic, phosphorous, aluminum, nitrogen and indium. Common material chemistries for LEDs are Gallium Arsenide (GaAs), Gallium Arsenide Phosphide (GaAsP), Gallium Aluminum Arsenide (GaAlAs), Indium Gallium Nitride (InGaN). Gallium nitride (GaN), Indium Gallium Aluminum Phosphide (InGaAlP), and Gallium Phosphide (GaP). Material chemistries that include GaN and InGaN are typically utilized to produce LEDs that emit blue (400 nm) and green (570 nm) light. InGaAlP chemistries emit light in the green (560 nm) to red (680 nm) region of the spectrum while GaAs and GaAlAs emit light in the red (660 nm) to near infrared (950 nm) region of the spectrum. LEDs can be purchased in encapsulated packages or in die form. Encapsulated packages have the benefit of providing mechanical robustness while reducing Fresnel losses associated with a die/air interface.

Figure 7:
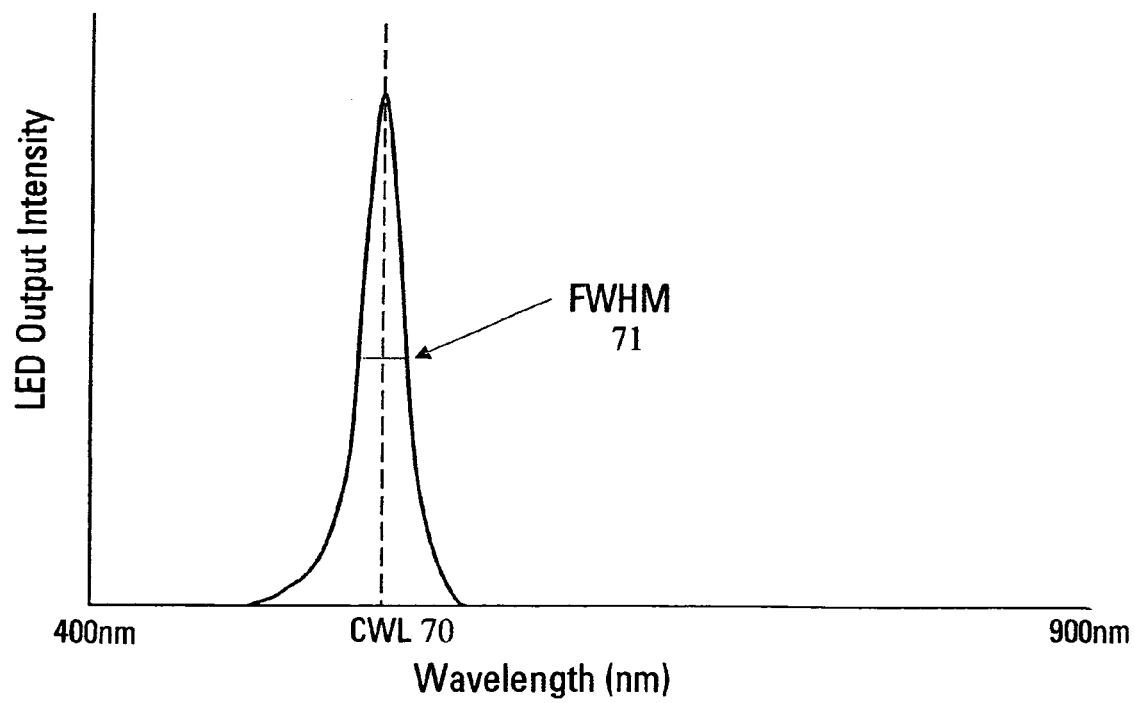
FIG. 7 illustrates the general shape of the emission spectrum for a monochromatic LED source.

LEDs are noncoherent light sources and their emission characteristic classified as being mostly monochromatic or quasi-monochromatic, that is, the frequencies composing the light are strongly peaked about a certain frequency, see FIG. 7. The spectral characteristic of an LED is defined by an emission band having a center wavelength 70 (CWL) and a spectral-line half-width 71. The center wavelength defines the peak emission wavelength of the LED and the spectral-line half-width defines the spectral bandwidth of the LED. However, a unique series of LEDs manufactured by Toshiba Corporation (Tokyo, Japan) exhibits a polychromatic spectral signature instead of a monochromatic signature. These LEDs are composed of a InGaAlP crystalline material with a GaAs substrate.

Figure 8:
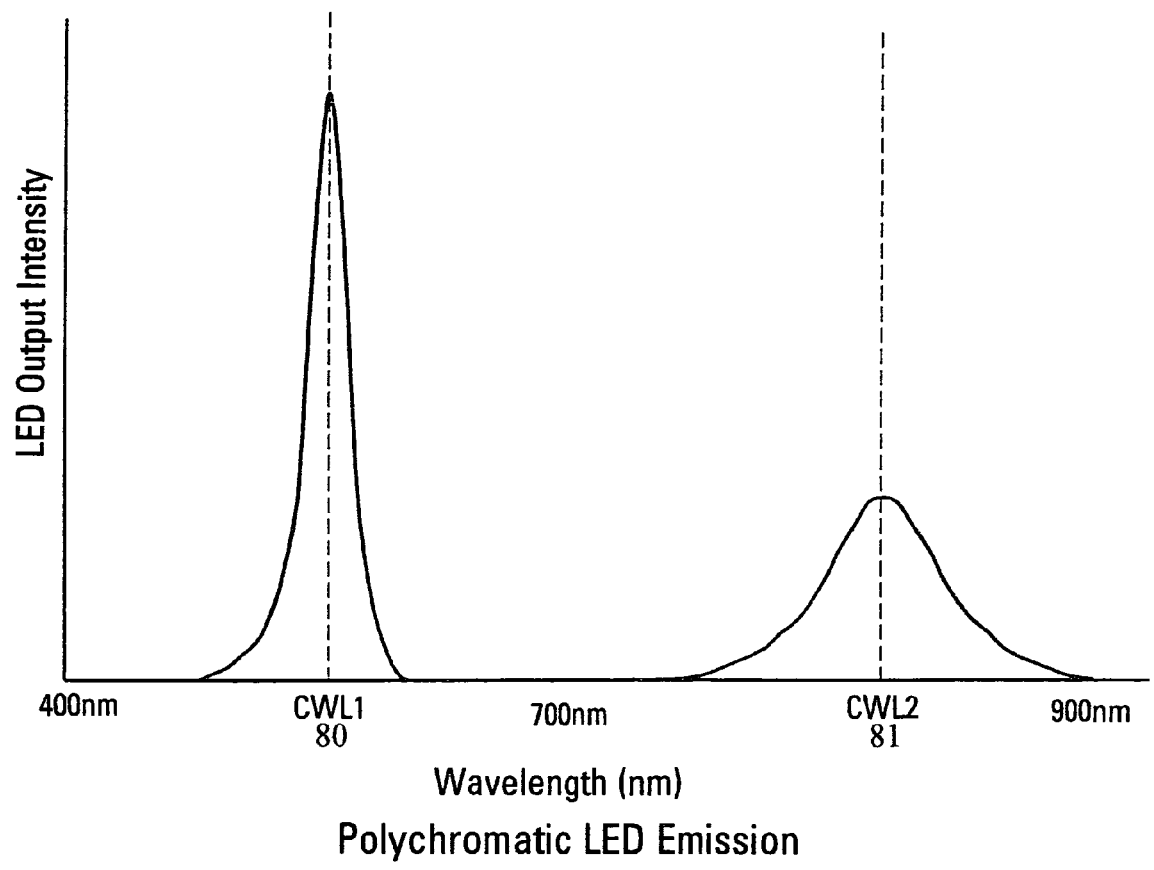
FIG. 8 illustrates the general shape of the emission spectrum for a polychromatic LED source.

The polychromatic characteristic curve for these devices is shown FIG. 8. Notice from the figure, that the emission characteristic is defined by two peaks one having a peak in the visible portion of the spectrum 80 (CWL1) and the other having a peak in the near infrared 81 (CWL2). For Toshiba LEDs, the visible peaks (CWL1) are available with peaks of 562 nm (TLPGE23TP), 575 nm(TLGE160), 595 nm (TLYH160), 612 nm (TLOH160) and 645 (TLRH160), nm with each having a second peak (CWL2) at about 840 nm. A light source such as this would be particularly suited for plant biomass measurements since the basic calculation for biomass requires a reflectance measurement in the visible region and a reflectance measurement in the NIR region. Using monochromatic LEDs technology requires two separate monochromatic LED sources and associated driver and compensation electronics, one in the visible and the other in the near infrared. However, to one skilled in the art, a psuedo polychromatic source of this invention can be constructed using multiple monochromatic sources modulated simultaneously. The advantage of the polychromatic light source is that for each reflectance sample taken, both IR and visible light sources illuminate the same region of the target (plant) being measured. Prior art devices alternately switch between sources monochromatic sources sequentially measuring different portions of the target (plant). For low speed, on-the-go sensor applications, this does impact the measurement to a high degree. But at high speeds, measured data can be skewed based on vehicle speed and the light channel sensing time with respect the portion of the canopy sensed.

Other embodiments of the present invention incorporate a polychromatic light source with additional monochromatic light sources. The polychromatic source is used to generate the NIR reflectance signal and visible reflectance signal and the monochromatic sources are utilized to generate reflectance signals pertaining to various pigment complexes in the plant and/or to stimulate chlorophyll fluorescence. As one can see, many combinations are possible with in the scope of this invention. In order to achieve good output stability with respect to thermal and aging effects, the LED sources should be adequately driven and monitored. The output intensity of LEDs is very temperature dependent. Depending on the material type, an LEDs output can drift between 0.4%/C and 1%/C. A decrease in output intensity, even it is being monitored and corrected via calculation, can result in diminished signal to noise performance of the measurement.

Figure 9:
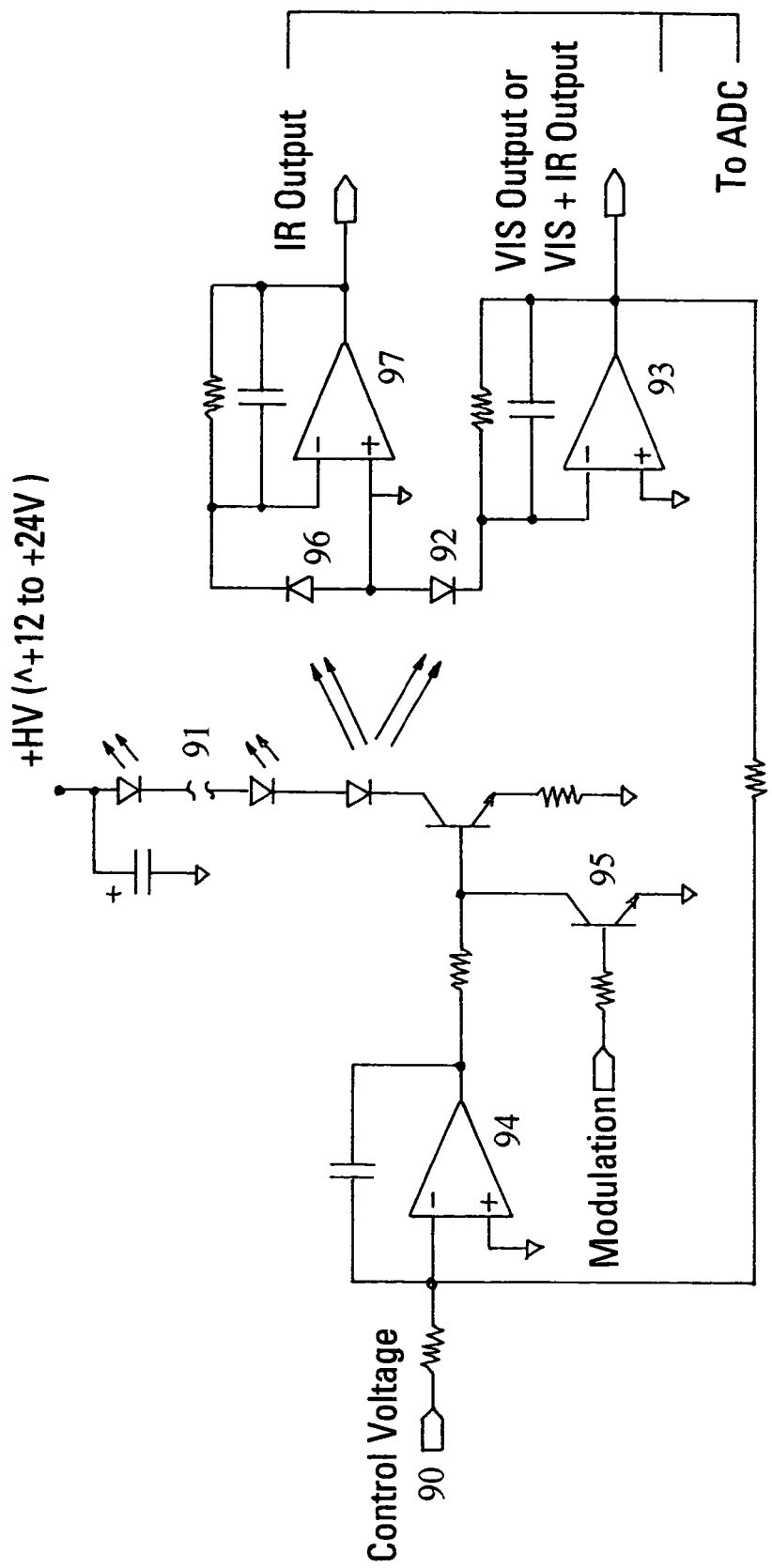
FIG. 9 shows schematically a circuit used to instrument the inventions light source.

FIG. 9 shows schematically a circuit that provides active power control for the light source and an output intensity signal for monitoring and calibration. Control voltage 90 sets the output power of light source 91. Photodiode 92, an Infineon SFH203 (Munich, Germany), samples part of the output intensity of light source 91 and feeds this signal via amplifier 93 to servo amplifier 94. Modulation of the output signal is performed using transistor 95. Furthermore, the output of amplifier 93 can be utilized to monitor the light source intensity for purposes of calibration and diagnostics. The performance of this circuit has provided output intensity control of approximately 0.05%/C over the operating range of the invention. When a polychromatic source is utilized, photodiode 96 and amplifier 97 incorporated into the circuit so as to monitor the IR output of the light source. Suitable photodiodes in this case would be a SFH203FA for photodiode 96 and a SFH203 for photodiode 92. Both diodes are manufactured by Infineon (Munich, Germany). Many techniques have been discussed in literature detailing methods on maintaining and stabilizing light sources for photometric type measurements including the method presented here.

Figure 10:
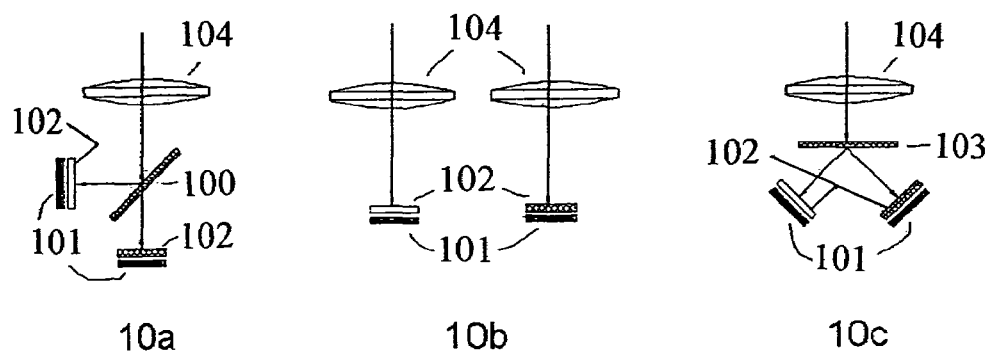
FIG. 10 illustrates several methods of detecting visible and infrared portions of the spectrum with a photodiode array.

The detectors used in the invention are most preferably silicon photodiodes however other detector technologies such as GaAsP, InGaAs, GaP, and the like, may be utilized as well. Silicon detectors have a typical photosensitivity spanning from 200 nm (blue enhanced) to 1200 nm. Band shaping of the detectors is performed using filtering materials such as colored filter glass, interference filters or dichroic filters. Combinations of the aforementioned filter techniques can be combined in order to band-shape the radiation impinging on the photodetector surface. For example FIG. 10a shows how a long pass edge filter or dichroic mirror 100 can be used to separate visible and infrared light. In this situation, one could choose to use a 750 nm long pass edge filter turned to a 45 degree angle to that of the incident light. Ideally, light having wavelengths less than 700 nm are reflected 90 degrees to that of the incident light and NIR light having a wavelengths greater than 700 nm pass through the filter. Additional trimming of the photodiodes can be achieved using narrow band interference filters or color glass 102 in front of the photodetectors 101. FIG. 10b shows another technique that utilizes narrow band interference filters or color glass 102 in front of the detectors 101 in order to reject off-band wavelengths. FIG. 10c shows the use a beam splitter 103 to split the incident light into two different components. Here, the incident light is split into two equal beams, directed toward detectors 101 having filters 102. In FIGS. 10a, b and c, the use of optional lenses or facilitating optics 104 to collect more optical energy are shown.

The motivation for wanting to minimize out of band light from reaching the photodetector is one to reduce photocurrent-generated noise. The higher the photo current, the higher the noise produced by the photodetector. The photocurrent-generated noise current ($i_{nl}$) is $$i_{nl} = \sqrt{2qBi_1}$$

where q is $1.6 \times 10^{19}$ Coulombs (C), B is the noise bandwidth in Hertz, and $i_l$ is the photocurrent in ampere (A).

One can see from the above equation as photocurrent rises, so does the noise associated with this current. Hence, reducing the intensity of the optical signal, or rather, reducing the out of band ambient light, the photodetector noise can be greatly improved. This is the technique that the present invention uses to improve the sensors noise performance. Prior art as taught in U.S. Pat. Nos. 5,296,702 and 6,596,996 make no attempt to reduce this type of out-of-band ambient light interference. Additionally, reducing the photodetector current by reducing the amount of measured ambient light also aids in reducing the effort by which ambient light levels are to be compensated allowing the detecting circuitry to operate over a much larger dynamic range of light intensities. Preamplifiers 64 in FIG. 6 amplify the output signals produced by the photodetectors. The typical embodiment of this invention uses a 2-detector array with one detector sensitive to light in the visible portion of the spectrum and the other sensitive to light in the infrared portion of the spectrum.

It should be obvious that additional detectors can be added to this array. For example, suppose the invention was required to measure reflectance at 595 nm, 670 nm, 880 nm and 1450 nm and was instrumented with the appropriate LED sources to do so. It is obvious from the above discussion that a single silicon photodiode will not be able to measure all the wavelengths listed. It does not have sensitivity past 1200 nm and an additional photodiode having a spectral sensitivity greater than 1450 nm is required. The solution to this problem is to add an InGaAs photodetector to the instrument in addition to the visible and NIR detector array. An InGaAs photodiode can have a sensitivity out past 2200 nm.

Figure 11:
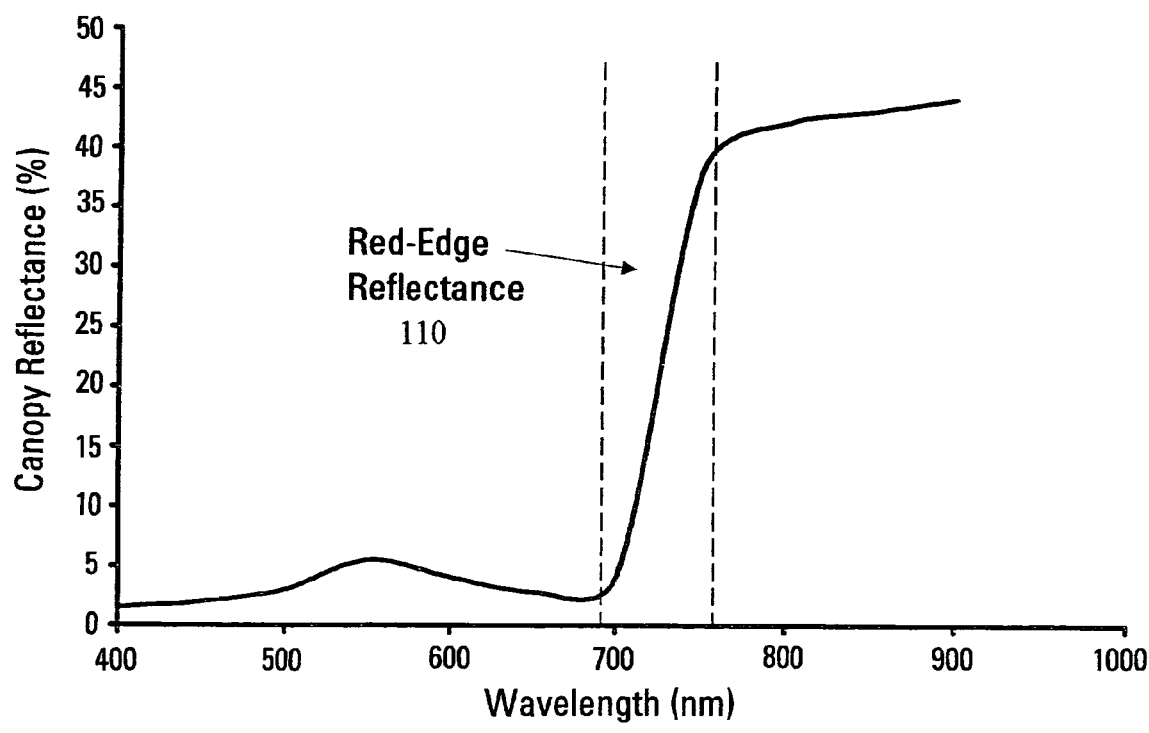
FIG. 11 shows a vegetative reflectance curve with the red-edge portion of the spectrum emphasized.

A unique embodiment of the invention involves the use of linear diode array detector and diffraction grating (or linear variable filter technology). The diffraction grating separates incoming, modulated light in to many wavelengths. If the modulated light source is chromatic in nature it will be composed of a broad number of wavelengths. One region of the particular interest on the vegetative reflectance curve in FIG. 11 is the so-called red edge 110 (~680 nm to ~760 nm). It has been reported in literature that the maxima of the derivative of the red edge bands is strongly correlated to the chlorophyll content of the plant. By configuring the present invention with a diffraction grating/linear array combination sensitive to this region of the vegetative reflectance curve, plant chlorophyll concentrations can be measured independent of soil background interference.

Referring once again to FIG. 6, the invention utilizes a phase sensitive detector circuit (PSD) 65 and analog-to-digital converter 66 (ADC) after each photodetector. The PSDs, also refer to as a lock-in amplifiers, are utilized by the invention to extract and further amplify the very small signal detected and amplified by the photodetector preamplifiers. PSDs are often used in applications where the signal to be measured is very small in amplitude and buried in noise. Detection is carried out synchronously with modulation of the light sources. Phase sensitive detection is one of many types of band narrowing techniques that can be utilized to measure small signals.

As will be apparent to those skilled in the art, other methods include the use of averaging techniques, discriminators and direct digital conversion/processing. With respect to direct digital conversion/processing, the phase sensitive acquisition component can be performed internally to a MCU or DSP by directly sampling the output of the photodiode amplifiers and performing the bandpass and PSD functions digitally. By performing these operations in the digital domain, the temperature drift of the phase detector, common to analog techniques, can be eliminated. The invention performs the synchronous modulation/demodulation at a carrier frequency of 250 kHz. It should be noted that the operation of the invention is not limited to this particular modulation rate and can operate at other modulation as well with as much effectiveness. Additionally, this rate can be increased or decreased as dictated by the application. The MCU or DSP samples the output of a PSD 65 utilizing ADC 66. The resolution of the ADC is most preferably 12 bits. Each channel can sampled using a dedicated ADC or one ADC can be utilized to sample all channels via a multiplexer.

Once the detected optical signals are amplified, demodulated and quantified, the MCU or DSP 67 can calculate a vegetative relationship based on the reflectance values sensed. Calculations of biomass can be performed using classic vegetative index calculations. There are many types of vegetative indices that can be used that are stated in scientific literature such as NDVI, TSAVI, $R_{700}/R_{NIR}$, etc . . . For example, a green pigment selective difference index (GPSDI) can be calculated using the equation listed as follows $$GPSDI = \left(\frac{R_{NIR} - R_G}{R_{NIR} + R_G}\right)$$

where $R_{NIR}$ is the measured infrared light (780 nm +/−5 nm) reflectance and RG is the measured green light (525 nm +/−15 nm) reflectance. The 525 nm source was utilized to excite chlorophyll fluorescence. The above relationship was utilized by the sensor in generating the data presented in Tables 1, 2 and 3.

Data calculated by the sensor's processing component is communicated to an operator or system controller via input/output interface 68. In the case of a handheld instrument, the I/O interface may take the form of a keypad and display. If the invention is incorporated into a sprayer or mapping system having several sensors networked together, the I/O interface will most preferably be a networkable serial port such a as RS485 port or CAN 2.0b port.

A general embodiment of the invention includes one or more banks of polychromatic LED sources having selected visible wavelengths chosen for a particular measurement band of interest. An alternate embodiment would have one or more banks of polychromatic sources and one or more banks of monochromatic sources. Additionally, the sensor would incorporate one or more banks of photodetectors selective to variety of visible and NIR bands and preferably matched to the spectral characteristics of the irradiating source and/or the fluorescent emission characteristics of the object being measured.

A typical embodiment of the sensor would include one or more banks of LEDs (at least one polychromatic LED bank with a combination of additional polychromatic and monochromatic banks) and two photodiode banks. One photodiode bank would be sensitive to light in the 400 nm to 700 nm range with the preferable lower limit equal to 500 nm and the preferable upper limit equal to 600 nm. The other detector bank would be sensitive to light in the 700 nm to 1000 nm range with the preferable lower limit equal to 700 nm and the preferable upper limit equal to 880 nm. For plant nitrogen deficiency and chlorophyll measurements, banks of 480 nm (monochromatic LED) and 590 nm (polychromatic LED: CWL 1 at 590 nm and CWL 2 at 840 nm) LEDs would be incorporated. The 590 nm polychromatic bank of LEDs would be used in the measurement of yellow light reflectance and while the blue 480 nm LED would be used to stimulate chlorophyll fluorescence. Additionally, the 590 nm LED bank would be used to measure plant biomass in the NIR region using CWL 2 at 840 nm. The photodiode bank sensitive in the 400 nm to 700 nm range would be used to measure yellow light reflectance from the plant canopy. The photodiode bank sensitive in the 700 nm to 1000 nm range would be used to measure chlorophyll fluorescence and 840 nm LED reflectance from the plant canopy. Additional wavelengths have been incorporated to measure subtle color differences with various pigment complexes in the blue green and red (500 nm to 670 nm) spectral regions.

Applications of Use-Methods

Figure 12:
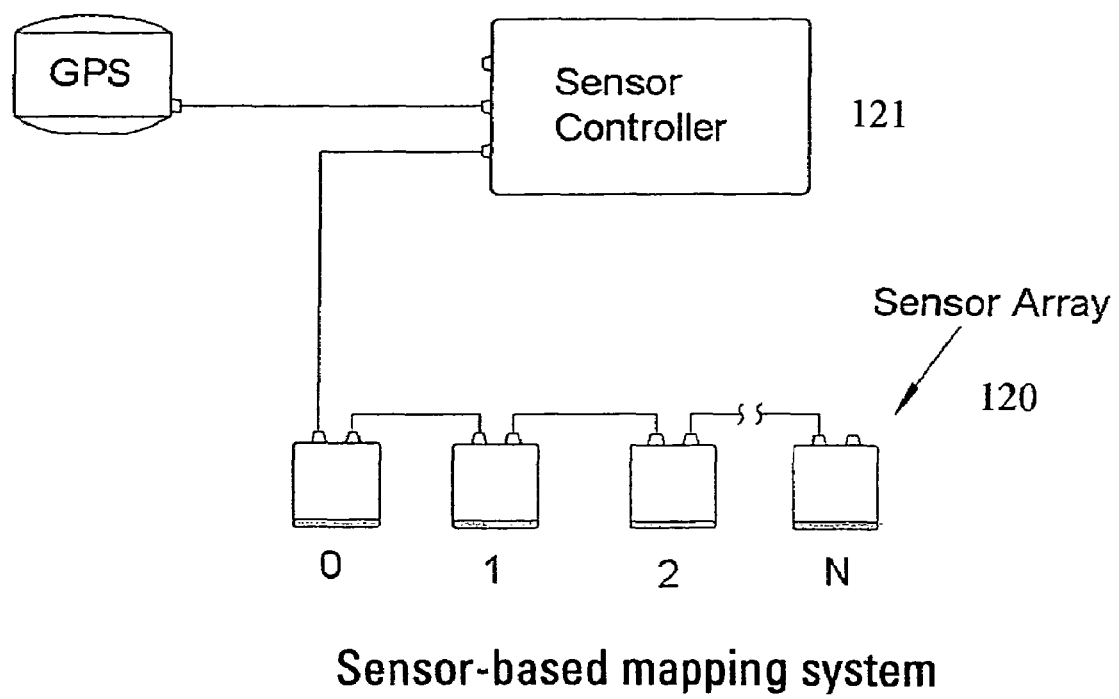
FIG. 12 shows diagrammatically a sensor based mapping system

FIG. 12 show a block diagram of the invention incorporated into a system that is used to mapped plant status. Elements of the system include sensor array 120, sensor controller 121, and GPS 122.

The role of the sensor in this system is to measure the biomass and/or biochemical properties of the plant being mapped. Data produced by the sensor is collected by the system controller for storage and later analysis. Each sensor point is geo-referenced using the GPS connected the system controller. There are two primary ways in which mapping can be performed the system. First, the map collected by the system can be all inclusive, that is, every data point measured by the sensor can be stored away in the controller's memory for later retrieval and analysis. Second, the sensor/controller can be programmed with a defined set of rules so as to distinguish poor performing regions of a landscape from good or healthy regions and vice versa and store only the poor performing regions. This mode of operation saves storage space in the controller and reduces the amount of data processing that has to be performed. As an example, the mapping systems could be mounted to the mower machinery for a golf course. When the course personnel perform their weekly mowing operations, the mapping systems would scout for problem areas of the turf. For turf management operations, this mode would be most useful because regions of turf that are suffering from stress (disease, water, nutrient, and so forth) or are beginning to suffer. The mapping systems would flag affected areas for the turf manager to scout out visually.

FIG. 13 show a block diagram of the invention incorporated into a system that is used for applying an agricultural product. Elements of the system include sensor array 130, sensor controller 131, GPS 132, fertilizer controller 133, sprayer pumps/actuators 134 and ground speed sensor 135.

The agricultural product may be either in liquid or solid form and may be, but not limited to, a nutrient, mineral, herbicide or fungicide or a combination of the aforementioned materials. The variable rate control system can be mounted to a commercial sprayer or tractor mounted sprayer system. GPS can be incorporated in the system when a map is required of plant canopy characteristics for later analysis. In addition, to mapping plant characteristics, material dispensation rates can be mapped as well. GPS is also required when applying fertilizer referenced to an N sufficient reference strip. In this situation, a region of the field is given an N-rate that totally meets the needs of the crop to grow without loss of yield and apply a lower amount of pre-emergent fertilizer (only the amount to initially cause the crop to grow) to the remainder of the field. At a time later in the growing season, the producer will apply a second treatment to the remainder of the field using the sensor readings for the N sufficient region of the field. Readings from the N insufficient parts of the field will be compared with readings from the N sufficient regions of the field. The controller will use the sensor measurements to calculate the appropriate rate of fertilizer to apply to the N insufficient portion of the field in order to prevent yield loss. FIG. 14 shows an applicator example with the sensor stood-off from the spray nozzles. When designing variable rate application system, the obvious approach is to physically locate the sensor close or next to the sprayer nozzle. However, because of the random orientation of most plant canopies the sensor should be separated from the sprayer nozzles by a distance D 140. This allows the sensing instrument to collect data on a portion of the crop, so as to average the spatial variability, before applying an agricultural product. The separation distance D between the sensor and sprayer nozzles should most preferably be greater than 3 feet. In operation, the variable rate system will collect data for D feet and apply an agricultural product over D feet while sensing the next D separation distance.

The benefits of a system such as the one just described are both economic and environmental. By using less fertilizer and only applying it where the crop needs it, the producer can lower his use of fertilizer and thus lower his production cost. Additionally, by using less fertilizer and only applying it where the crop needs it, reduced run-off and leaching into our watershed occurs. For weeding applications, the system controller uses the invention to detect weeds on roadways or in fields. Upon detection of a weed, the controller then causes the activation of a sprayer valve which dispenses herbicide on the weed. Because only the weed is sprayed, the amount of herbicide is conserved and not wasted on bare soil or ground.

Because the present invention produces its own source of light, the measurements that it makes is not influenced by ambient light conditions. Applicator equipment fitted with sensors of this type can be operated around the clock at night and under full sun. Spraying herbicide at night has some significant advantages because cooler conditions allow longer and more effective working hours at critical times during season. Specifically, the higher relative humidity at night aids foliage wetting, thereby prolonging the efficacy of the herbicide material, and the absence of wind after sunset eliminates over-spraying. Therefore, in addition to significantly reducing the cost of herbicide associated with the elimination of weeds, the present invention, by having the capability of operating at night, provides additional advantages.

A particularly useful application for the present invention is in the area handheld instrumentation for research and field scouting. In this application the sensor electronics are enclosed in an easy in to hold housing. The instrument in this configuration can be used to measure plant characteristics ranging from 1 foot to 7 feet. The embodiment would most preferably be utilized to scout to measure turf biomass or turf color. The invention fitted with a red polychromatic LED array, a green LED and blue LED could be used to measure turf biomass (NDVI) and turf color (RGB). This instrument would allow turf professionals an objective way in which to measure the color and quality of the turf surface. Currently, turf color is measured using a subjective measure that utilizes a color grading scale. Turf color is compared to colored cards and is assigned a number between 0 and 9.9 based on the comparison.

Another embodiment of the handheld invention is one that has the ability to measure the concentrations of leaf pigments such as chlorophylls (chl a and chl b), anthocyaninds, and carotenoids via reflectance and/or fluorescence measurements. Pigment content and photosynthesis are often linked to other leaf physiological and structural properties; thus, it is possible to infer a number of critical plant properties from leaf pigment content and composition such as stress, nitrogen content, functional type, senescence, etc . . . Conventional techniques (paper chromatography, thin layer chromatography and high-performance liquid chromatography) have many drawbacks that severely restrict their use. These limitations include high cost (both instrumental and operational costs) and the long time required for extraction and quantification, and sample destruction. It is clear that wet chemical extraction is not possible or desirable under many circumstances.

Non-destructive techniques, based on measuring the transmitted and reflected radiation from plant leaves, have the potential of evaluating the physiological status of plants. Transmittance and reflectance spectroscopy offers one alternative to destructive and time-consuming wet chemical extraction. Chlorophylls, carotenoids, and anthocyanins are positioned for light absorption in particular wavebands and can readily be assessed with spectral absorption and reflectance.

Chlorophylls are the most important of photosynthetic pigments and are virtually essential for the oxygenic conversion of light energy to the stored chemical energy that powers the biosphere. From a physiological perspective leaf chlorophyll content is a parameter of significant interest. From an applied perspective, chlorophyll content is important for several reasons. First, the amount of solar radiation absorbed by a leaf is largely a function of the chlorophyll and low concentrations can directly limit photosynthetic potential and hence primary production. Second, much of leaf nitrogen is incorporated in chlorophyll, so quantifying their concentration gives an indirect measure of plant status. Last, pigmentation can be directly related to stress physiology. Chlorophylls generally decrease under stress and during senescence.

Carotenoids are the second major group of plant pigments. Carotenoids can absorb incident radiation and contribute energy to the photo synthetic system. The fraction of photosynthetically active radiation absorbed by a plant canopy (faPAR) has been related to net primary productivity as a function of a light use efficiency coefficient defining the carbon fixed per unit radiation intercepted. The photosynthetic potential of two plants may differ even though their faPAR is equal, depending upon the concentrations of individual pigments. Furthermore, when incident radiation exceeds that needed for photosynthesis, carotenoids that compose the xanthophyll cycle dissipate excess energy and protect the photochemical reaction centers.

Anthocyanins are the third major group of pigments in leaves. Anthocyanins can modify the light environment within a leaf and have a potential to regulate photosynthesis and limit photo inhibition and photo bleaching thereby having a photo protective function.

In this embodiment, the sensor electronics are housed in a small, handheld leaf clip that can be clamped onto a leaf. The sensor clamp can either connect to a handheld readout terminal or have a means for displaying measurements directly on its console. Alternately, the sensor may be housed in such a fashion to facilitate on the go measurements e.g. mounted to a high-clearance vehicle or similar agricultural equipment. Additionally, an external port will be included on the counsel to allow connection of GPS hardware to the instrument. The added flexibility of GPS capabilities will allow data to be geo-referenced within experimental test sites, crop production sites, turf sites, and the like.

Although only a few exemplary embodiments of this invention have been described in detail above, those skilled in the art will readily appreciate that many modifications are possible in the embodiments given without materially departing from the novel teachings and advantages of this invention. Accordingly, various modifications, adaptations, and combinations or various features of the described embodiments can be practiced without departing from the scope of the invention as set forth in the claims.

What is claimed is:

1. A light sensor for measuring the reflectance of an object, comprising:
   (a) a polychromatic light source simultaneously emitting visible light and infrared light with a modulator of the light source, and apparatus to set and monitor optical power of the light source;
   (b) a reflected light receiver comprised of an array of photodetectors comprised of at least one photodetector sensitive to visible light positioned to receive reflected light originating from the light source and including ambient light compensation means for reducing the effects of ambient light on the photodetector and a first output, and at least one photodetector sensitive to nonvisible light positioned to receive reflected light originating from said light source and including an ambient light compensator for reducing the effects of ambient light on said second photodetector and a second output;

(c) a detector for distinguishing the light originating from the light source and light reflected by the object from ambient light; and (d) a computational device for performing calculations based on reading the first output, reading the second output and the light source power.

2. A light sensor as defined in claim 1, wherein the light source is comprised of two or more distinct light emitters selected from the group consisting of quasi-monochromatic light emitters, polychromatic light emitters, monochromatic light emitters, and combinations thereof.

3. A light sensor as defined in claim 2, wherein each light emitter is modulated at the same frequency in synchrony with the other light emitter or emitters.

4. A light sensor as defined in claim 1, further comprising at least one quasi-monochromatic or monochromatic light emitter.

5. A light sensor as defined in claim 1, further comprising spectral selectivity means, and wherein the ambient light compensator further comprises a diffraction grating and wherein said reflected light receiver receives light from the diffraction grating.

6. A light sensor as defined in claim 1, further comprising spectral selectivity means, and wherein the ambient light compensator further comprises a linear variable filter and wherein said reflected light receiver receives light through the linear variable filter.

7. A light sensor as defined in claim 1, wherein the photodetector array is a linear photodiode array or linear CCD array.

8. A light sensor as defined in claim 1, wherein the photodetector array is comprised of imaging detectors.

9. A light sensor as defined in claim 1, wherein the object comprises a plant.

10. A light sensor as defined in claim 9, further comprising an applicator responsive to the computational device for applying a product to the plant.

11. A light sensor as defined in claim 10, wherein the applicator is separated from the light receiver by 3 feet or more.

12. A light sensor for measuring the fluorescence of a plant, comprising:

(a) a polychromatic light source simultaneously emitting visible light and infrared light with a modulator of the light source, and apparatus to set and monitor optical power of the light source;

(b) a reflected light receiver comprising a first photodetector sensitive to light between about 690 nm and about 720 nm and positioned to receive emitted light originating from the plant due to the excitation by the light source; an ambient light compensator for reducing the effects of ambient light on the first photodetector; and a first output; a second photodetector sensitive to light between about 720 nm and about 780 nm positioned to receive emitted light originating from the plant due to excitation by the light source; an ambient light compensator for reducing the effects of ambient light on the second photodetector; and a second output;

(c) a detection means for distinguishing the light originating from the light source and emitted by the plant from ambient light; and (d) a computational device to calculate a measurement based on reading the first output and reading the second output and light source power.

13. A sensor as defined in claim 12, wherein the sensor measures reflectance and fluorescence.

14. A light sensor for measuring the reflectance of an object, comprising:

(a) a solid-state polychromatic light source emitting light simultaneously in the visible spectrum and the infrared spectrum, a means of modulation of the light source, and a means to set and monitor optical power of the light source;

(b) a reflected light receiver comprising a first photodetector sensitive to visible light positioned to receive reflected light originating from the light source, ambient light compensation means for reducing the effects of ambient light on the first photodetector; and a first output, a second photodetector sensitive to nonvisible light positioned to receive reflected light originating from said light source, and ambient light compensation means for reducing the effects of ambient light on said second photodetector; and a second output;

(c) a detection means for distinguishing the light originating from said light source and reflected by an object from ambient light; and (d) a computational device to perform a calculation based on reading said first output, said second output and said light source power.

15. A method for measuring the reflectance of a plant, comprising the steps of:

(a) simultaneously projecting light of a first, visible wavelength from a solid-state polychromatic light source and light of a second, infrared wavelength from the light source, modulating the light source, and setting and monitoring optical power of the light source;

(b) receiving reflected visible light originating from the light source in a reflected light receiver comprising a first photodetector sensitive to visible light, and reducing the effects of ambient light on the first photodetector in an ambient light compensator; and a first output;

(c) positioning a second photodetector sensitive to infrared light to receive reflected infrared light originating from the light source, and reducing the effects of ambient light on said second photodetector in an ambient light compensator; and a second output;

(c) distinguishing the light originating from said light source and reflected by the object from ambient light; and (d) calculating in a computational device a vegetative index based on reading said first output and said second output and light source power.

16. A method as defined in claim 15, wherein the light source is comprised of a at least two light emitters, the first light emitter emitting light of wavelengths between about 450 nm and about 645 nm and the second light emitter emitting light of wavelengths in the near infrared, and wherein the calculation of the vegetative index correlates to plant biomass, plant chlorophyll content, plant pigment content or combinations thereof.

17. A method as defined in claim 15, wherein the light source is comprised of at least two light emitters, the first light emitter emitting light of red, blue and green wavelengths and the second light emitter emitting light of wavelengths in the near infrared, and wherein the calculation of the vegetative index corresponds to plant color, plant biomass or combinations thereof.

18. A light sensor for measuring the reflectance of an object, comprising:

(a) a single light source that simultaneously illuminates a substantially identical area with both visible and nonvisible light with a modulator of the light source, and apparatus to set and monitor optical power of the light source;

(b) a reflected light receiver comprised of an array of photodetectors comprised of at least one photodetector sensitive to visible light positioned to receive reflected light originating from the light source and including ambient light compensation means for reducing the effects of ambient light on the photodetector and a first output, and at least one photodetector sensitive to nonvisible light positioned to receive reflected light originating from said light source and including an ambient light compensator for reducing the effects of ambient light on said second photodetector and a second output;

(c) a detector for distinguishing the light originating from the light source and light reflected by the object from ambient light; and (d) a computational device for performing calculations based on reading the first output, reading the second output and the light source power.

* * * * *